United States Patent
Kalachev et al.

(10) Patent No.: US 7,692,145 B2
(45) Date of Patent: Apr. 6, 2010

(54) METHOD TO ANALYZE PHYSICAL AND CHEMICAL PROPERTIES ON THE SURFACE LAYER OF A SOLID

(76) Inventors: Alexei Alexandrovich Kalachev, Arndt Str. 19, D-12489 Berlin (DE); Nikolai Mikhailovich Blashenkov, pr. Nastavnikov, d.5,korp.3,kv.12, 195298 Sankt-Peterburg (RU); Yuri Petrovich Ivanov, ul.B. Porokhocskaya, d.32, kv.27, 195176 Sankt-Peterburg (RU); Vladimir Antonovich Kovalsky, ul.Metallistov, d.25, korp.3, kv.100, 195176 Sankt-Peterburg (RU); Alexandr Lvovich Myasnikov, ul.Petropavlovskaya, d.8, kv.24a, 197022 Sankt-Peterburg (RU); Lyubov Petrovna Myasnikova, ul. Chaikovskogo, d.63, kv.11, 191123 Sankt-Peterburg (RU)

( * ) Notice: Subject to any disclaimer, the term of this patent is extended or adjusted under 35 U.S.C. 154(b) by 297 days.

(21) Appl. No.: 11/957,603

(22) Filed: Dec. 17, 2007

(65) Prior Publication Data

US 2008/0237488 A1   Oct. 2, 2008

Related U.S. Application Data

(63) Continuation of application No. 10/527,966, filed on Oct. 20, 2005, now Pat. No. 7,309,864.

(30) Foreign Application Priority Data

Jul. 15, 2003   (WO) .................... PCT/RU03/00311

(51) Int. Cl.
   *G01N 25/02* (2006.01)
(52) U.S. Cl. .................. 250/310; 374/17; 374/161; 422/52
(58) Field of Classification Search ............... 422/52; 374/17, 161; 250/310
See application file for complete search history.

(56) References Cited

U.S. PATENT DOCUMENTS

| | | | | | |
|---|---|---|---|---|---|
| 3,317,727 | A | * | 5/1967 | Medlin | 250/337 |
| 4,638,163 | A | * | 1/1987 | Braunlich et al. | 250/337 |
| 4,873,444 | A | * | 10/1989 | Cooke et al. | 250/337 |
| 4,906,848 | A | * | 3/1990 | Braunlich et al. | 250/337 |
| 5,683,179 | A | * | 11/1997 | Lowry | 374/17 |
| 5,998,146 | A | * | 12/1999 | Latva et al. | 435/6 |
| 6,200,531 | B1 | * | 3/2001 | Liljestrand et al. | 422/52 |
| 6,509,701 | B1 | * | 1/2003 | Rakhimov et al. | 315/363 |
| 6,517,777 | B2 | * | 2/2003 | Liljestrand et al. | 422/52 |
| 6,639,360 | B2 | * | 10/2003 | Roberts et al. | 313/512 |
| 6,652,810 | B1 | * | 11/2003 | Ziegler | 422/82.08 |
| 6,979,829 | B2 | * | 12/2005 | Calvert et al. | 250/472.1 |
| 7,067,072 | B2 | * | 6/2006 | Chen | 252/301.6 S |

* cited by examiner

Primary Examiner—David A. Vanore
(74) Attorney, Agent, or Firm—John D. Gugliotta, PE, Esq.

(57) ABSTRACT

The present invention relates generally to a method for analyzing the surface and the near-surface layers of a solid and, more specifically, to a method that utilizes activating actions to analyze the physical and the chemical properties of the layers. The instant abstract is neither intended to define the invention disclosed in this specification nor intended to limit the scope of the invention in any way.

10 Claims, 13 Drawing Sheets

METHOD TO ANALYZE PHYSICAL AND CHEMICAL PROPERTIES ON THE SURFACE LAYER OF A SOLID

RELATED APPLICATIONS

The present application is a Continuation of U.S. Ser. No. 10/527,966 (now U.S. Pat. No. 7,309,864) and claims the benefit of an Oct. 20, 2005 filing date. The present Application incorporates the subject matter of ('966) as if it were fully rewritten herein.

BACKGROUND OF THE INVENTION

1. Field of the Invention

The present invention relates generally to a method for analyzing the surface and the near-surface layers of a solid and, more specifically, to a method that utilizes activating actions to analyze the physical and the chemical properties of the layers.

2. Description of the Related Art

Physical and chemical properties vary substantially between a surface or a near-surface layer of a solid and the bulk of its structure. In many respects, the properties comprised for the surface layer govern the behaviors of the solid in different media and in the fields of various forces. A basic understanding of these properties paves the way for scientifically based modifications of the surface layer for the purposes of scientific and medicinal progress. Information obtained from an analysis of the surface layer additionally provides a means for industries to control the surface quality of products with a greater precision. Examples of industries include those in the fields of protective coatings, microelectronics or nanoelectronics.

It is important that the surface layer of a solid is preserved for the purposes of analyzation. The present invention teaches a method to preserve and to analyze a surface layer. A search of the prior art revealed no references that teach the claims of the present invention; however, the steps taught in U.S. Pat. No. 5,683,179 to Lowry are related.

Lowry discloses a method to detect the conductive state in an energized superconductor. Lowry teaches the following consecutive steps: (1) cooling a superconducting device to a preselected operating temperature; (2) activating a thermoluminescent sensor by irradiating the sensor with periodic pulses at a preselected radiation; and, (3) energizing the superconducting device by means of heating the sample. Lowry utilizes well-known and classic methods of thermoluminescense to accomplish the protection of superconductive devices. The activation steps taught in the present method alternatively vary in order and in quantum to preserve the surface layer of a solid for the purpose of analyzing the properties.

A method for analyzing physical properties of the surface layer of a solid is known, involving the activation of the surface layer of a solid by low-temperature plasma (LTP) followed by deactivation of the surface layer during which a thermoluminescence spectrum is recorded. The LTP used in this method is ignited by an unmodulated voltage with a frequency of 40.68 MHz at a 10-Pa pressure of a plasma-generating gas, the duration of the sample activation by LTP being from 10 s to 9 min (see A. A. Kalachev, etc., "Plasma-induced Thermoluminescence—a New Method for Investigating Supramolecular Architectures and Temperature Transitions in Polymers and Other Solid Surfaces", Applied Surface Science 70/71 (1993), pp. 295-298 (a copy is attached)).

This engineering solution is taken as a prototype of the variant of the method as per claim 3 of the present invention.

The disadvantage of the prototype method is a modifying influence of the LTP with said parameters upon the surface layer of the sample investigated, which results in insufficiently reliable information on physical and chemical properties of this layer. First of all, this is due to strict plasma parameters used in the prototype, namely, a high pressure of a plasma-generating gas (10 Pa) and relatively long (10 s and more) duration of plasma activation. Both factors lead to overheating of the surface layer and a decay of arising active states already in the course of plasma treatment. For example, as seen from FIG. 4 of the prototype, the luminescence intensity typically falls with increasing treatment time. Moreover, said strict plasma parameters lead to other physical-chemical changes in the surface layer being analyzed.

In addition, in the mode of isothermal luminescence (see FIG. 3, paper by A. A. Kalachev etc.) the curves obtained according to the known method and illustrating the dependence (decrease) of thermoluminescence on time from the moment the LTP activation of the sample is over have no characteristic features; therefore, during this period of time no useful information on the surface structure or surface physical-chemical processes was obtained using said method. The curves are only used as a means for the determination of the moment when heating aimed at deactivation of the surface layer of a solid has to be started.

SUMMARY OF THE INVENTION

It is an object of the present invention to preserve the surface layer of a solid to achieve a more accurate and a more informative analysis of the physical and the chemical properties comprised for the surface layer. It is an object of the present invention to achieve the foregoing object by means of a decrease in the modifying influence if irradiation. It is envisioned that a single pulse of irradiation activates the surface layer in the present method. The methods known in the art utilize a continuous, pulsed radiation to activate a sample. These known methods undesirably modify the surface layer because particles are constantly charged and the analysis is conducted while particles are in excited states; however, an advantage to the present invention is that the surface layer doesn't undergo these repeated bombardments and, as such, the transition parameters of a sample are not compromised.

It is a second object of the present method to deactivate a surface layer by keeping the solid at a constant temperature so that data can be recorded for the loosely coupled states of the surface layer. It is a third object of the present invention to then heat the solid for the purposes of obtaining data on the thermoluminescence spectrum of the surface layer.

It is a further object of the present invention that a single pulse of irradiation will provide a means to analyze radiation spectra after the particles are charged rather than while the particles are being charged. It is an object that the quanta emitted from the deactivation of a surface layer activated by a single pulse of irradiation, between $10^{\wedge}-5$ to $10^{\wedge}-3$ W/cm$^2$, is more accurate and more reliable because the irradiation influence is considerably weaker.

BRIEF DESCRIPTION OF THE DRAWINGS

The advantages and the features of the present invention will become better understood with reference to the following more detailed description and the claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the Figures.

Figure 1:
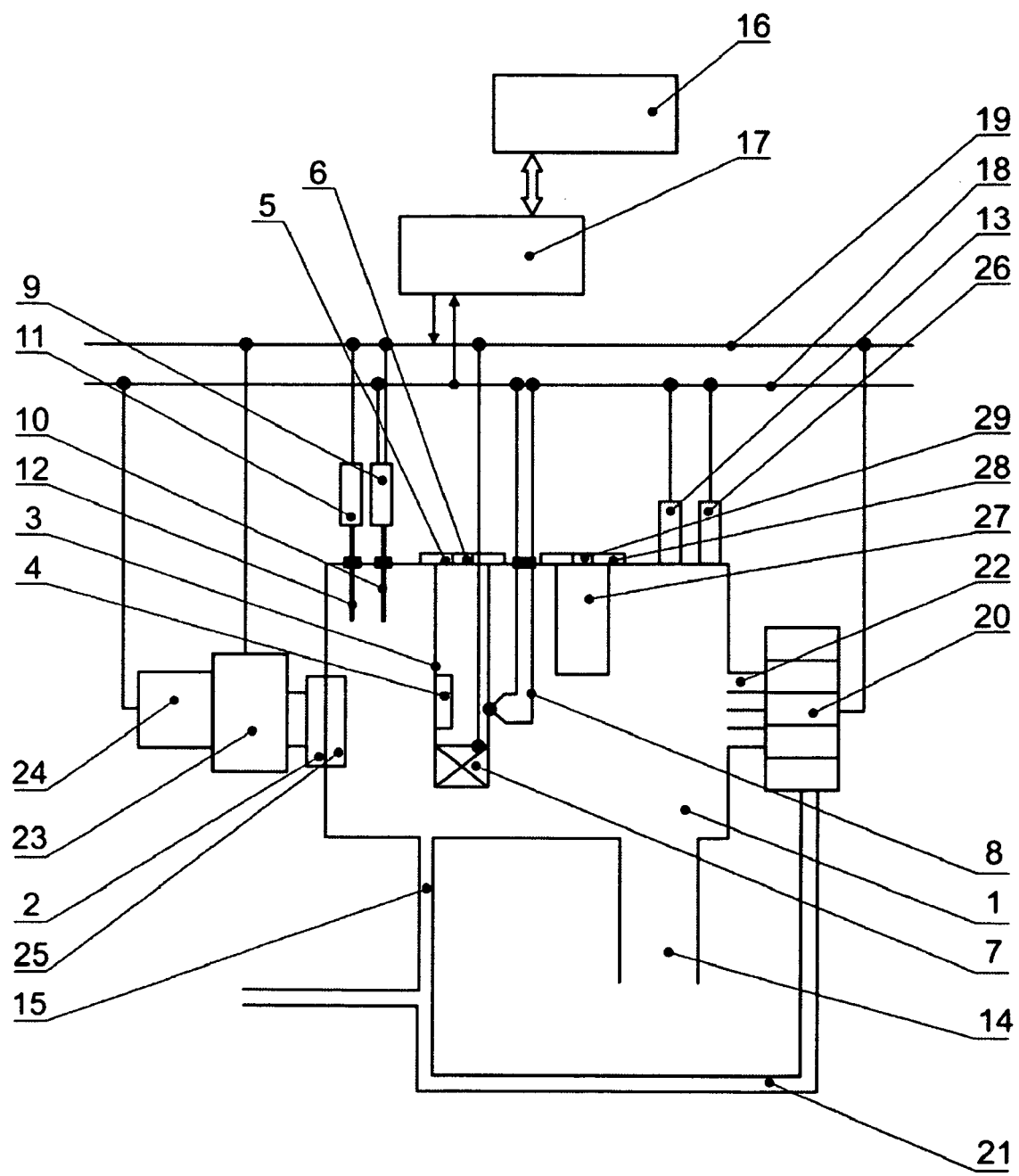
FIG. 1 is a schematic diagram of the device used to implement the method of the present invention.

It is important that some description be given to the manner and to the practice of the device utilized to perform the present method. A device utilized in the present method is shown in FIG. 1. The device comprises a stainless steel vacuum chamber 1 equipped with an optical window 2 made of quartz. The vacuum chamber 1 comprises a copper container 3 to hold a sample 4 of solid. Springs (not shown) may be utilized to fix the sample 4 to an outer surface of the container 3. A lid 5 covers the container, but an orifice 6 comprised on the lid 5 provides a means for a coolant, in particular liquid nitrogen, to be fed into it. A heater 7 is located in the container 3 and a chromel-alumel thermocouple 8 is placed on its outer surface.

A generator 9 comprised on the device produces electromagnetic oscillations with a frequency approximating 16 MHz. An electrode 10 comprised on the generator 9 inserts into the vacuum chamber 1. A high-voltage transformer 11 initiates electric discharge and, more specifically, it delivers 20-kV pulses from a secondary winding upon the closing-breaking of a circuit of a primary winding. The pulses are applied to an electrode 12 located in the vacuum chamber 1.

The electric discharge duration is set by a timer (not shown). A "barotron"-type gauge 13 comprised on the outer surface of the vacuum chamber 1 communicates with it. A main 14 comprised on the vacuum chamber 1 decreases the pressure to approximately $1.33 \times 10^{-5}$ Pa. A second main 15 delivers gases to the vacuum chamber. It is preferred that hydrogen is the gas delivered, but other inert gases may be utilized, s.a., oxygen, nitrogen, etc.

Information obtained for the purposes of analyses is analyzed by means of a computer 16 comprised on the device. The computer system includes an interface 17 placed between the computer 16 and a data acquisition bus 18. The interface 17 comprises an AD-7858 analog-to-digital converter, an AD8080 microprocessor and a source of voltages for the different blocks of the device which are supplied to the bus 18.

An atomizer 20 comprised on the device generates an atom and/or a molecular and/or an ionic and/or an electronic and/or a photon beam. In a given embodiment, the atomizer 20 is in the form of aggregate capillaries, 20 µm in diameter, that form a narrow beam. To generate a molecular beam, a main 21 delivers gas while the capillaries, an ion gun, an electron gun and a DRSH-100 mercury lamp generate a photon beam.

The atomizer 20 also comprises a means to form pulses of the above mentioned beams. An output 22 of the atomizer 20 is coupled to the vacuum chamber 1. A means to analyze the wavelengths of light emitted by the surface of the sample 4 is positioned between the means to detect the emitted light and the sample 4. In a given embodiment, the means to analyze the wavelengths comprises an MDR-3 monochromater 23 with a PHEU-68 photomultiplier 24 connected to its output. In particular cases, light filters may alternatively be used instead of the monochromator 23. The monochromator 23 is placed in front of the outer surface of the optical window 2, which is shielded by a screen 25 placed inside the vacuum chamber 1. A PMI-2 gauge 26 attached to the outer surface of the vacuum chamber 1 controls the pressure within the vacuum chamber 1.

Finally, the device comprises a trap 27 provided as means to feed the coolant. The trap 27 is placed in the vacuum chamber 1.

1. Detailed Description of the Figures

The method according to the preferred embodiment of the present invention is herein disclosed. A sample 4 is placed into the vacuum chamber 1. Air is evacuated from the vacuum chamber 1 through the main 14 until the pressure is $1.33 \times 10^{-5}$ Pa. The trap 27 is filled with coolant, which results in the adsorption of residual gases and water vapors on its surface. The optical window 2 is cut off from the radiation of the vacuum chamber 1 by means of the screen 25.

When the necessary commands are issued from the computer 16 to generate an a beam, the surface layer of the sample is subjected to a pulse of the beam or to successive pulses of different beams. Simultaneously, hydrogen is fed into the atomizer. It is preferred that the total irradiation power per unit of area on the investigated surface layer lies within the range of 10^-5 to 10^-3 W/cm².

Following the step or irradiation, the sample is kept at a constant temperature. A spectrum of energy quanta, in particular light, emitted by the surface layer is recorded. The monochromator 23 and the photomultiplier 24 are utilized to analyze the wavelengths and to detect the intensity of the light emitted. This information is sent to the computer for further processing.

The sample is heated by means of the heater 7 in the next step to the present method. The temperature is controlled by means of the thermocouple 8, wherein the signals from the thermocouple 8 and the photomultplier 24 are sent to the computer for further processing.

2. Operation of the Preferred Embodiment

EXAMPLE 1

Single Pulse to Sample of Low-pressure Polyethlene

Figure 2:
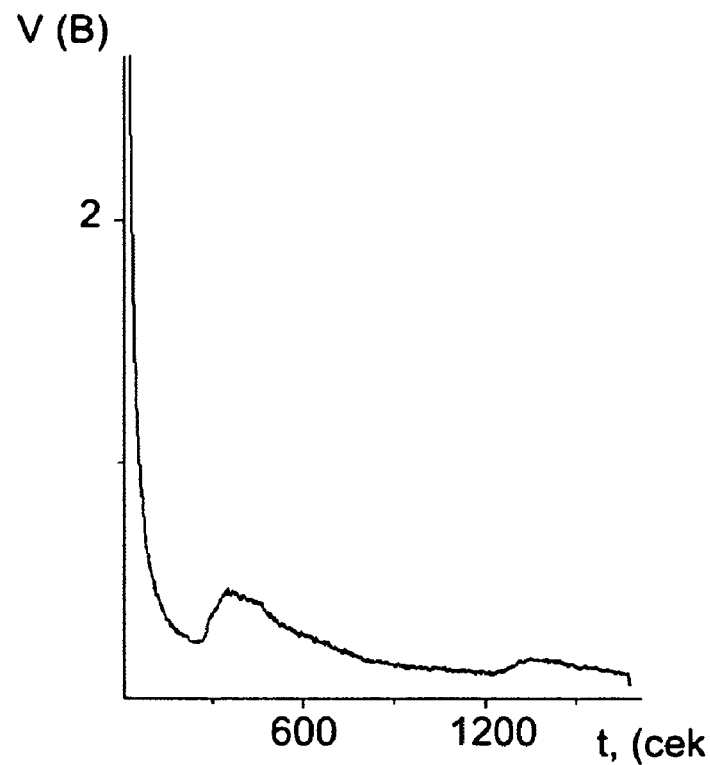
FIG. 2 shows a constant-temperature spectrum of the light emitted by a sample surface activated by an atom beam.

The surface layer of a low-pressure polyethlene, MOPLEN ($M_w$=114000) was subjected to a pulse of a hydrogen atom beam to activate the particles. The irradiation power per a unit of area investigated on the surface was $2 \times 10^{-5}$ W/cm². The recorded constant-temperature spectrum of the energy quanta emitted by the surface of the polyethylene sample is presented in FIG. 2. The graph exhibits two maxima that provide information on the loosely coupled states of the surface layer and the half-lives of these states.

Figure 3:
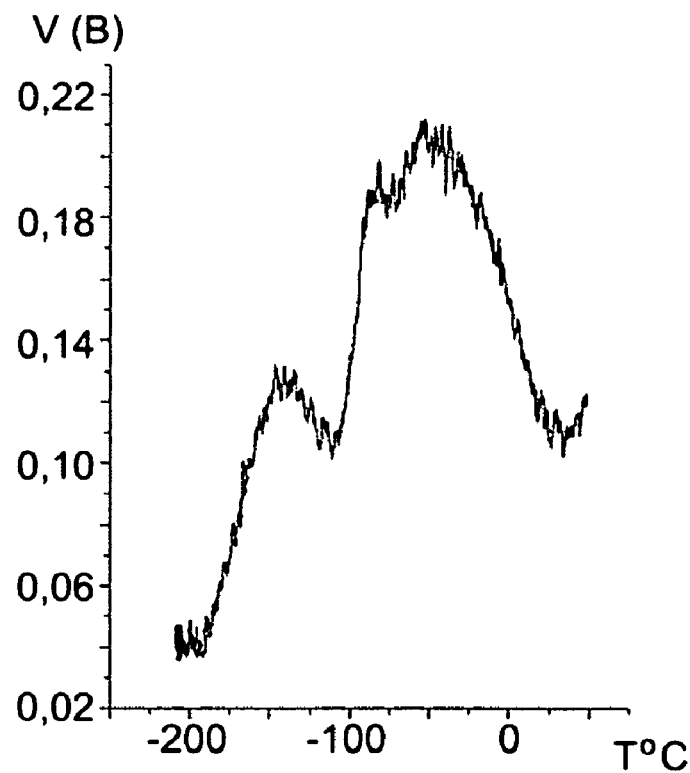
FIG. 3 shows a spectrum of the light emitted by a sample surface activated by an atom beam and then heated.

A thermoluminescence spectrum recorded when the sample was heated is shown in FIG. 3. The thermoluminescence spectrum provides information on the phase and the relaxation temperatures of the investigated surface layer.

EXAMPLE 2

Single Pulse to Sample of a Quenched Polyethylene

Figure 4:
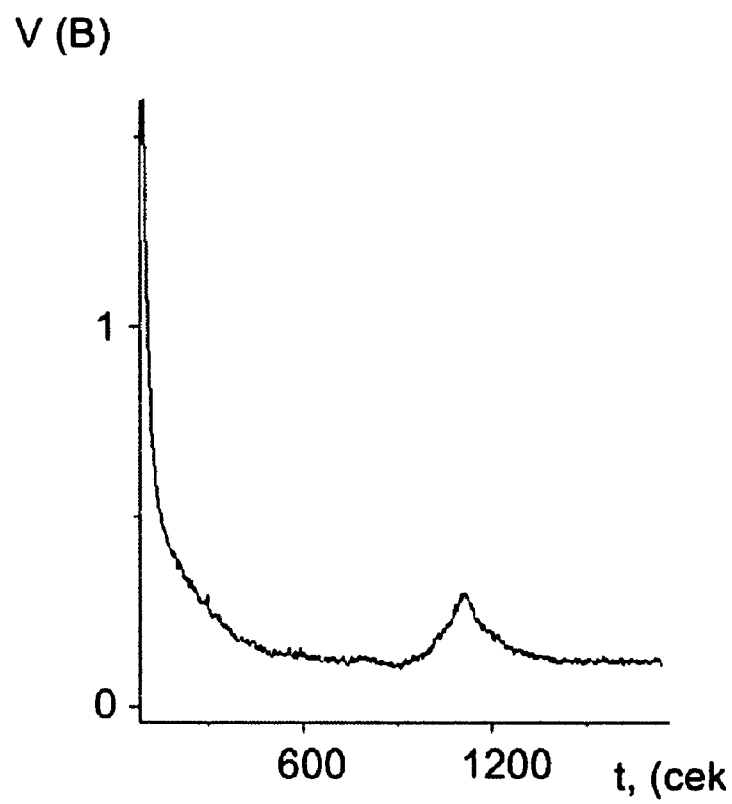
FIG. 4 shows a constant-temperature spectrum of the light emitted by a sample surface activated by an atom beam.
Figure 5:
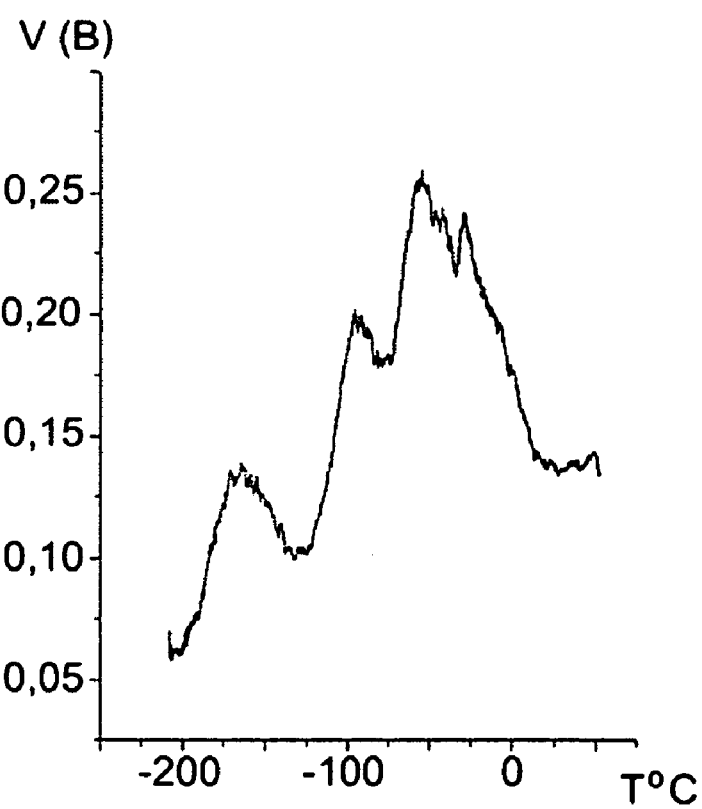
FIG. 5 shows a spectrum of the light emitted by a sample surface activated by an atom beam and then heated.
Figure 6:
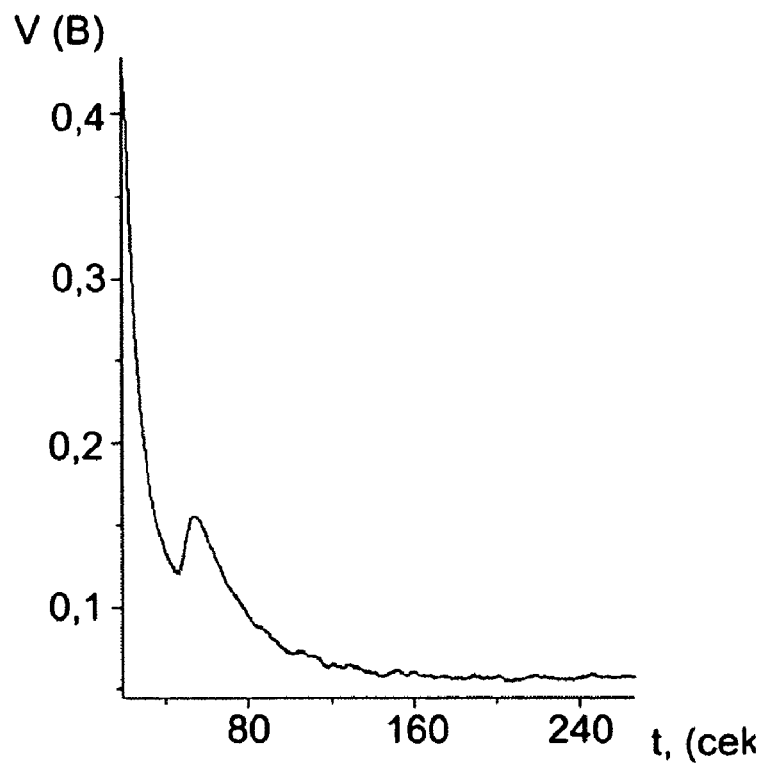
FIG. 6 shows a constant-temperature spectrum of the light emitted by a sample surface activated by an atom beam.
Figure 7:
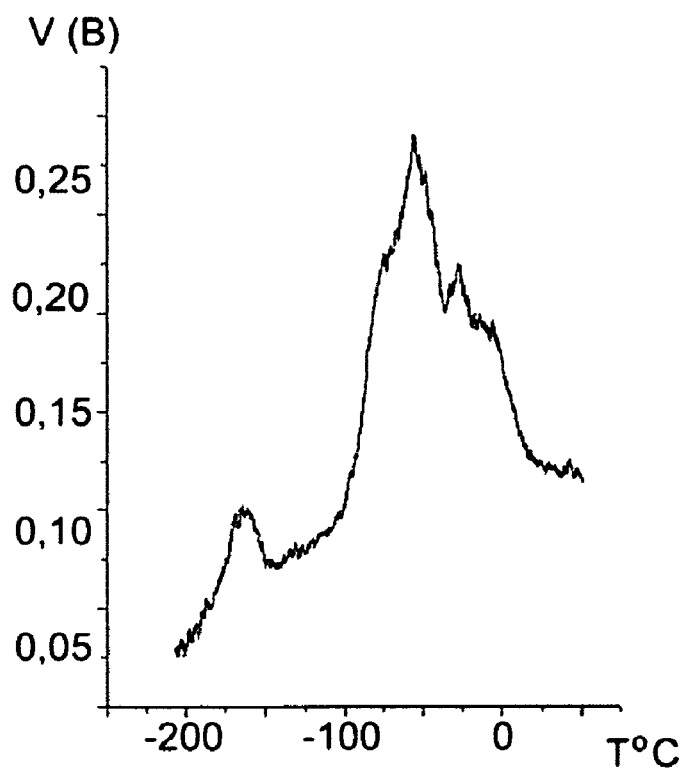
FIG. 7 shows a spectrum of the light emitted by a sample surface activated by an atom beam and then heated.
Figure 8:
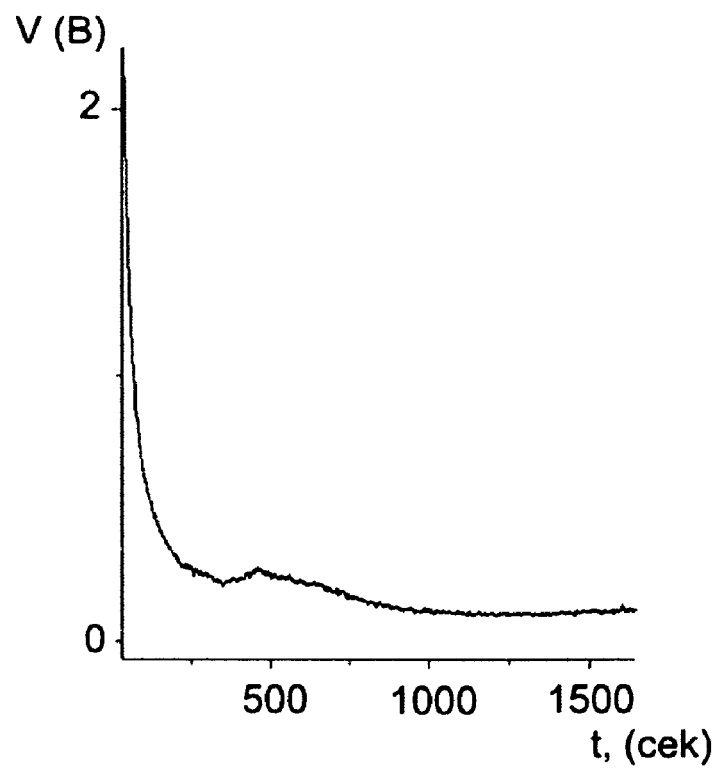
FIG. 8 shows a constant-temperature spectrum of the light emitted by a sample surface activated by a molecular beam.
Figure 9:
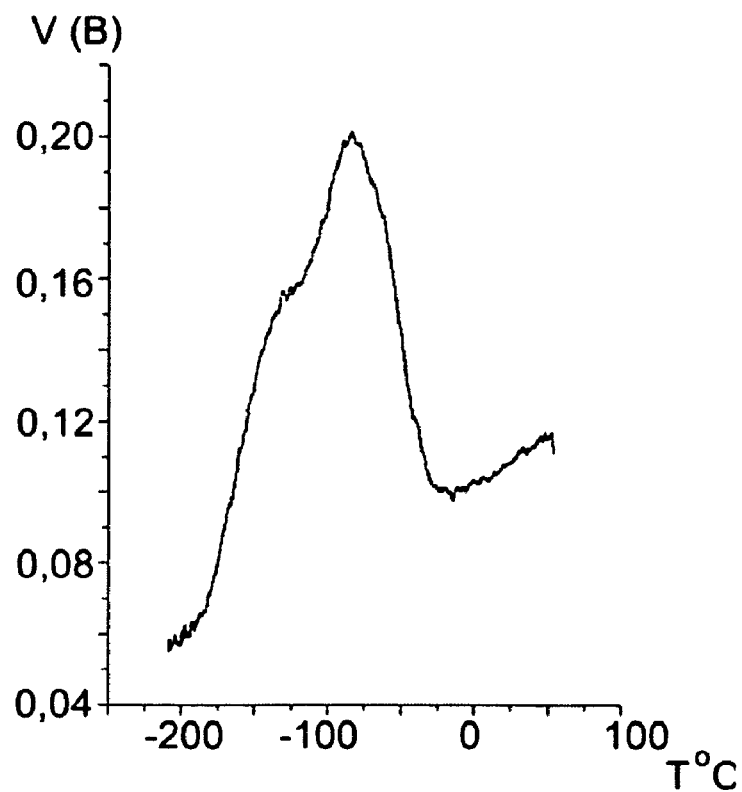
FIG. 9 shows a spectrum of the light emitted by a sample surface activated by a molecular beam and then heated.
Figure 10:
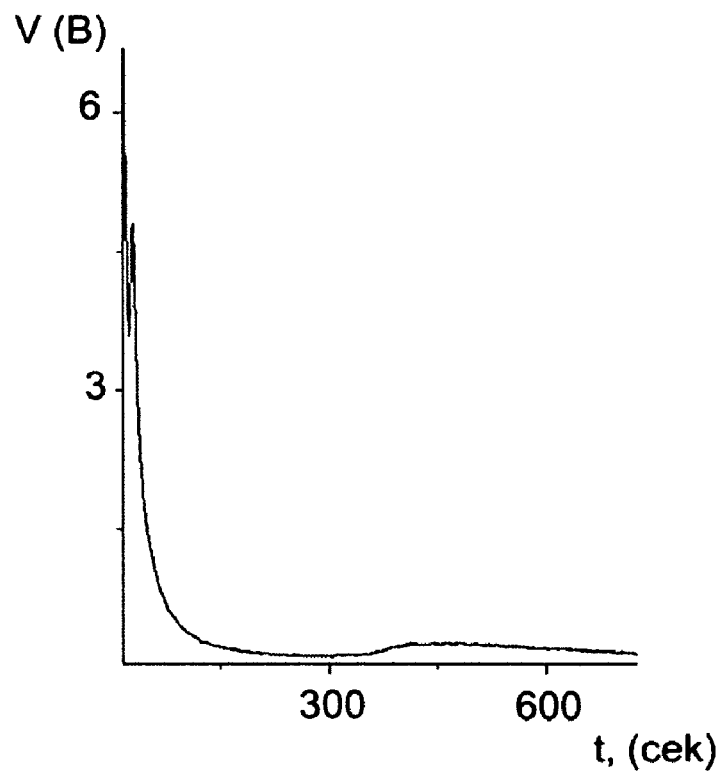
FIG. 10 shows a constant-temperature spectrum of the light emitted by a sample surface activated by an ion beam.
Figure 11:
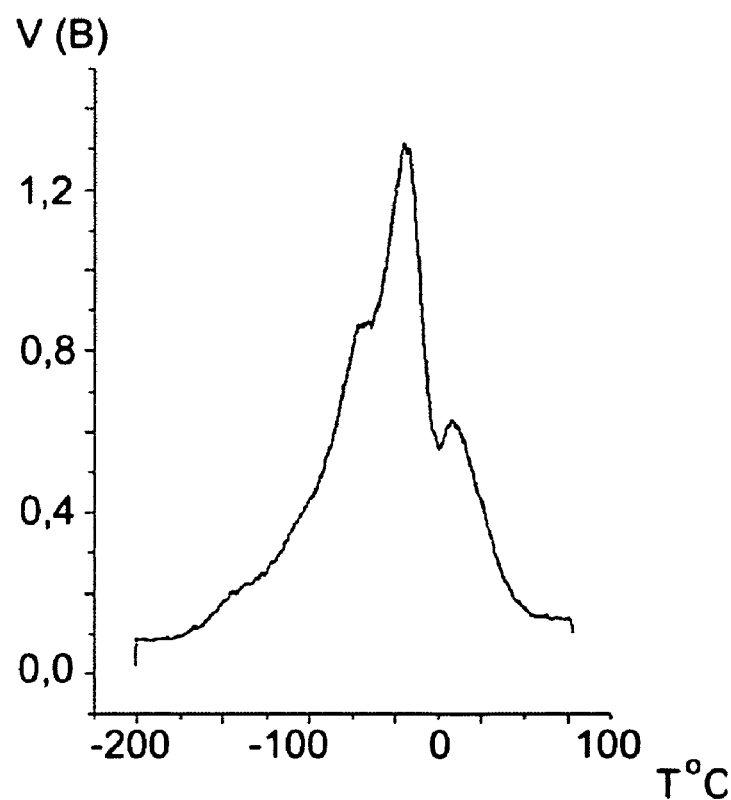
FIG. 11 shows a spectrum of the light emitted by a sample surface activated by an ion beam and then heated.
Figure 12:
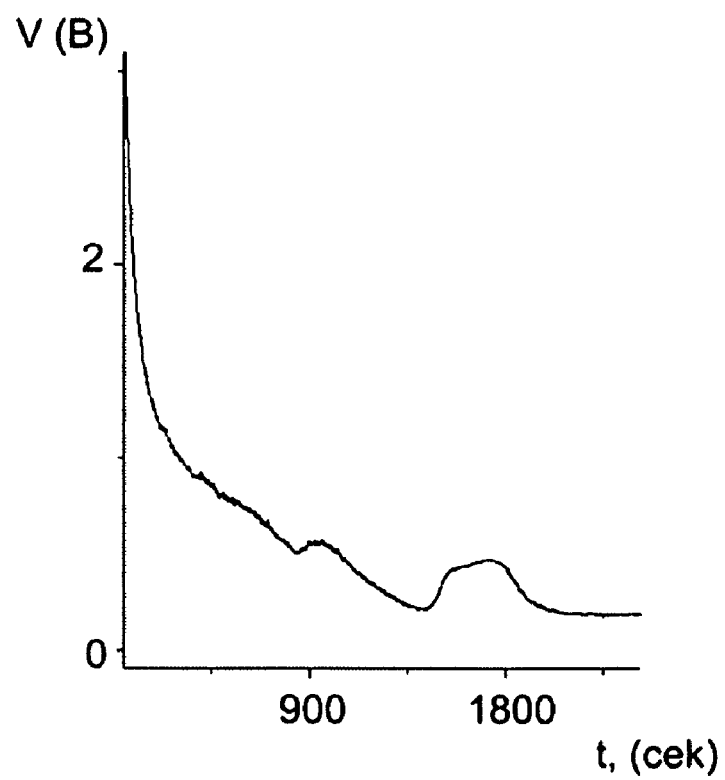
FIG. 12 shows a constant-temperature spectrum of the light emitted by a sample surface activated by a photon beam.
Figure 13:
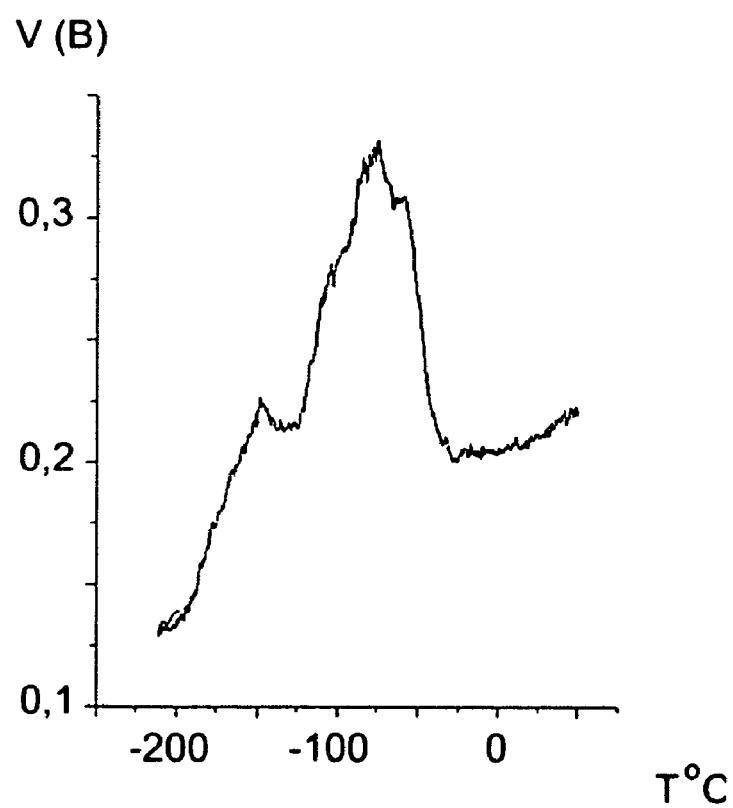
FIG. 13 shows a spectrum of the light emitted by a sample surface activated by a photon beam and then heated.

A sample of a quenched polyethylene of the same grade was irradiated under the same conditions as in Example 1. The spectra of the light emitted by the surface layer is presented in FIGS. 4 and 5.

A comparison of the spectra emitted by one and the same materials, but prepared under different conditions, reveals a considerable difference in the properties of the surface layers.

EXAMPLE 3

Successive Pulses to Sample of a Quenched Polyethylene

A sample of a quenched polyethylene of the same grade was irradiated. The surface layer of the sample was successively subjected to unit pulses of the following beams: electron, molecular, ion and photon. The spectra of the light emitted from the surface layer were consecutively recorded at a constant temperature and during the heating stage. The spectra are shown, respectively, in FIGS. 6-13. The total irradiation power of the four above mentioned unit pulses was $10^{-3}$ W/cm² per a unit of area investigated on the surface. Each type of irradiation excited definite states in the surface layer of the sample, making it possible to more thoroughly and accurately characterize the various physical and chemical properties of the layer. Some of the properties analyzed include the phase and the relaxation transition temperatures, the activation energies of these transitions, the half-lives of loosely coupled surface states, the chemical reactions occurring on the surface, the orders of reactions, etc.

The known dependencies were used to infer information on the properties of the surface layer from the radiation spectra. The following ration is used to determine the activation energy of relaxation transition (Ep).

$$Ep = \frac{RT_{max}^2}{T' - T_{max}}$$

The equation includes the following variables:

R is the gas constant;

T' is the temperature of the high-temperature wing of the thermoluminescence maximum at which the thermoluminescence is half the maximum intensity; and, $T_{max}$ is the temperature at which the maximum thermoluminescence is observed.

The order of the chemical reaction giving rise to isothermal luminescence is inferred from the dependence of the light emission intensity at a constant temperature in the coordinate systems ln I-t or ln I-1/t², wherein I is the luminescence intensity and t is the time. If the dependence is linear in the former system, the chemical reaction is of the first order (decomposition). If the dependence is linear in the latter system, the chemical reaction is of the second order (recombination).

EXAMPLE 4

Successive Pulses to Sample of Low-pressure Polyethylene

Figure 14:
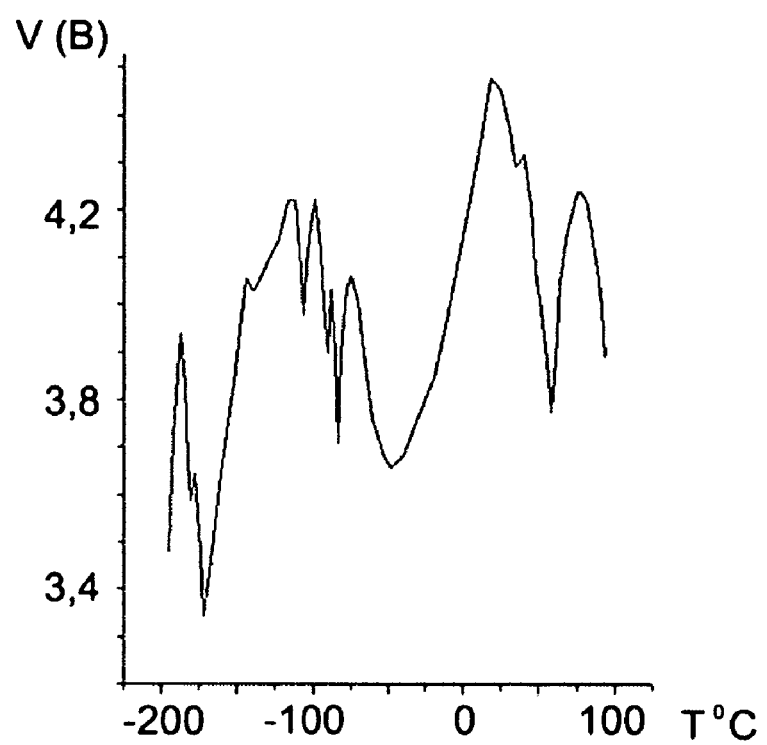
FIG. 14 shows a spectrum of the light emitted by a sample surface activated successively by an atom, an electron, a molecular, an ion and a photon beam and then heated.

The overall effects of successive irradiation to the surface layer of the low-pressure polyethylene studied in Example 1 was recorded for atom beams, electron beams, molecular beams, ion beams and photon beams. The total irradiation power of the pulses was $5 \times 10^{-5}$ W/cm² per a unit of area investigated on the surface. FIG. 14 shows the a thermoluminescence spectrum recorded when the sample was heated. The spectrum exhibits multiple peaks that give information on the relaxation temperatures and the energies of phase and relaxation transitions. FIG. 14 differs from the thermoluminescence spectra recorded for a sample separately irradiated by unit pulses of the above mentioned beams. Each type of irradiation excites definite states in the sample surface layer. The states previously excited by some irradiation react to another irradiation differently, which bases any conclusion for the properties of a surface layer on combined irradiations.

EXAMPLE 5

Successive Pulses to Sample of Low-pressure Polyethylene

Figure 15:
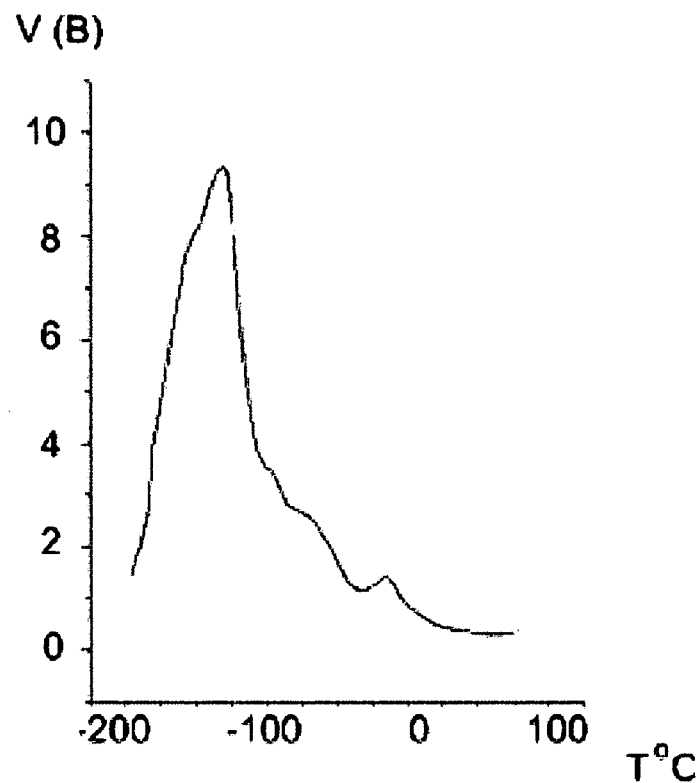
FIG. 15 shows a spectrum of the light emitted by a sample surface activated successively by an atom, an electron, a molecular, an ion and a photon beam and then heated.

The overall effect of successive irradiation to the surface layer of a sample of low-sample polyethylene, the sample of which was produced similar to that of Example 4, was investigated for electron, photon and ion beams. The total irradiation power of the pulses was $3.7 \times 10^{-5}$ W/cm² per a unit of area investigated on the surface. FIG. 15 shows a thermoluminescence spectrum recorded for the surface layer when the sample was heated.

EXAMPLE 6

Successive Pulses to Sample of Low-Pressure Polyethylene

Figure 16:
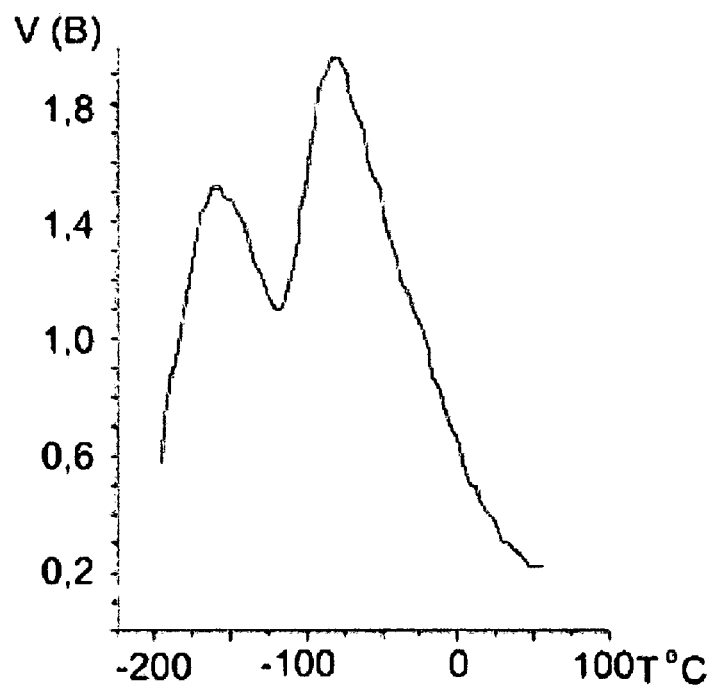
FIG. 16 shows a spectrum of the light emitted by a sample surface activated successively by an electron, a photon and an ion beam and then heated.

The overall effect of successive irradiation to the surface layer of a sample of low-sample polyethylene, the sample of which was produced similar to that of Examples 4 and 5, was investigated for electron, photon and ion beams. The total irradiation power of the pulses was $3.2\times10^{-5}$ W/cm$^2$ per a unit of area investigated on the surface. FIG. 16 shows a thermoluminescence spectrum recorded for the surface layer when the sample was heated.

EXAMPLE 7

Successive Pulses to Sample of Low-pressure Polyethylene

Figure 17:
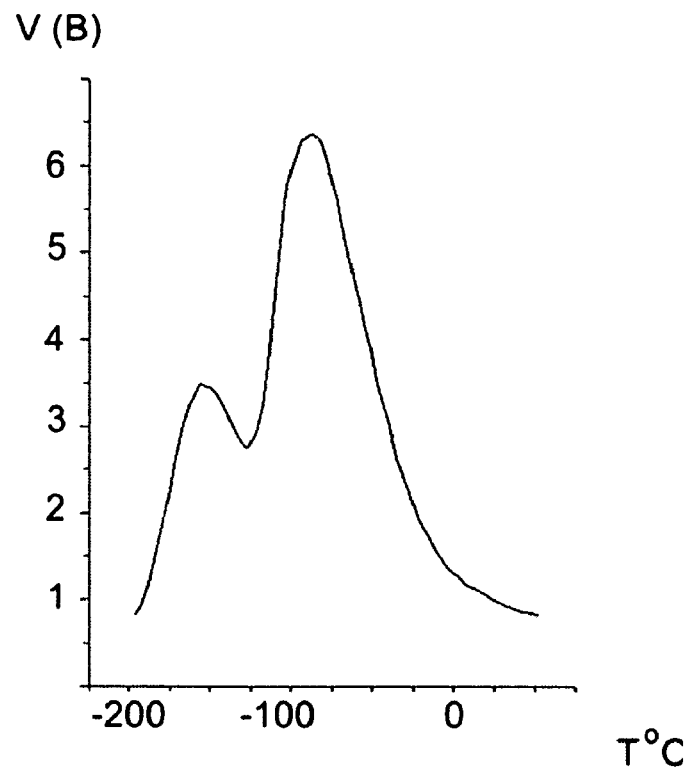
FIG. 17 shows a spectrum of the light emitted by a sample surface activated successively by an atom and an ion beam and then heated.
Figure 18:
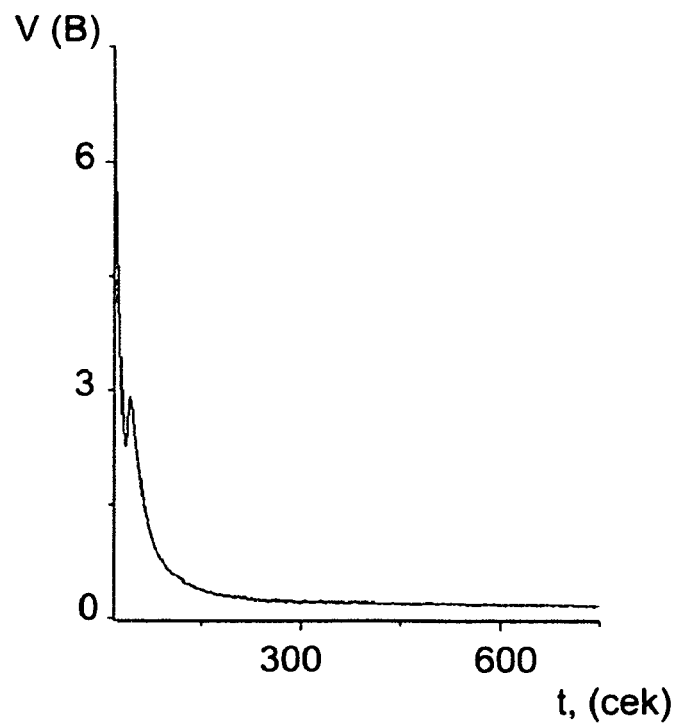
FIG. 18 shows a constant-temperature spectrum of the light emitted by a sample surface activated by low temperature plasma.
Figure 19:
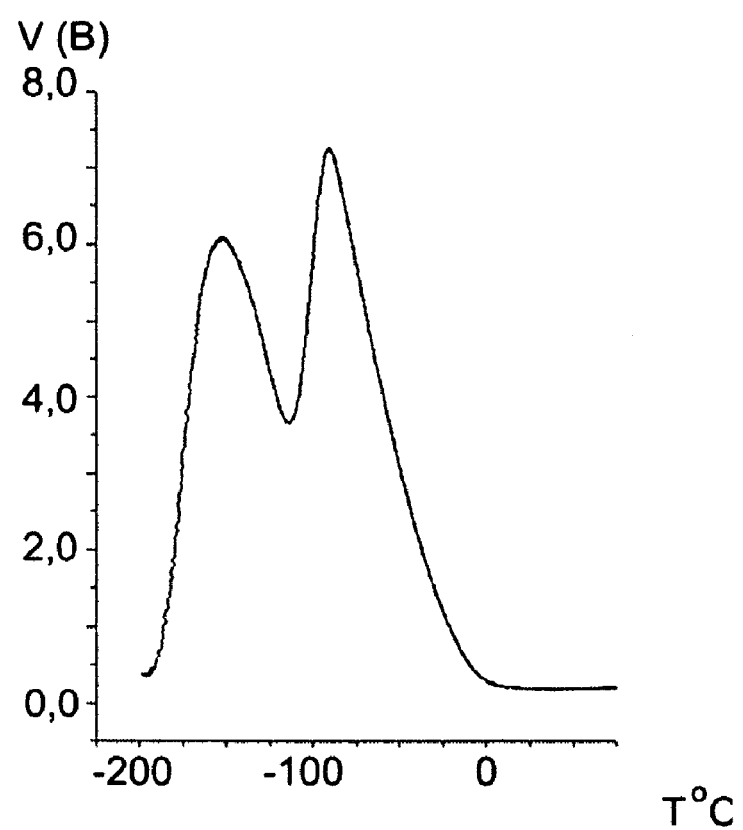
FIG. 19 shows a spectrum of the light emitted by a sample surface activated by low temperature plasma and then heated after emittins shown in FIG. 18 is completed.
Figure 20:
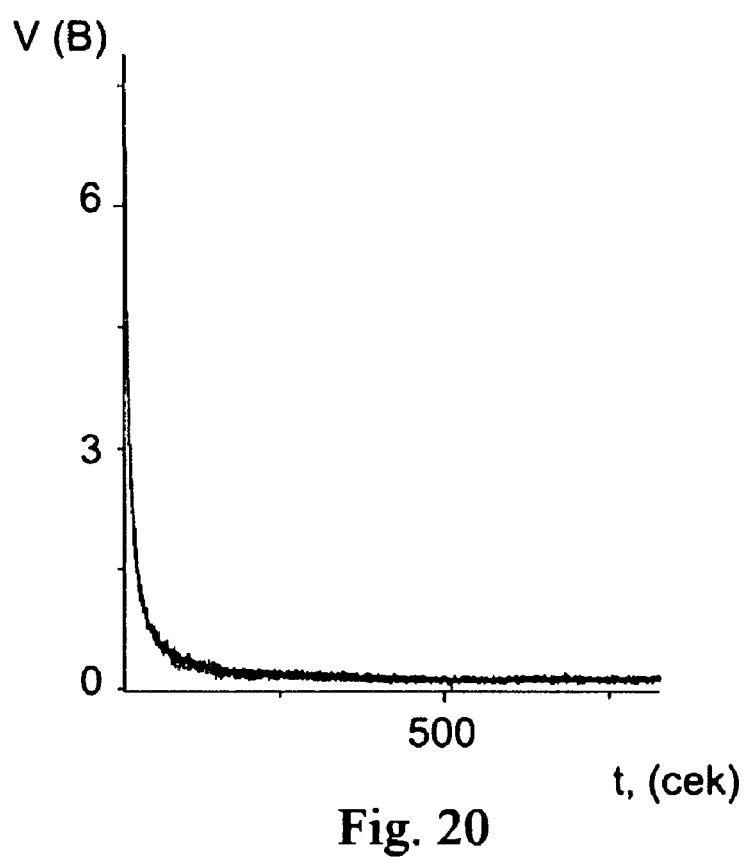
FIG. 20 shows a constant-temperature spectrum of the light emitted by a sample surface activated by low temperature plasma.
Figure 21:
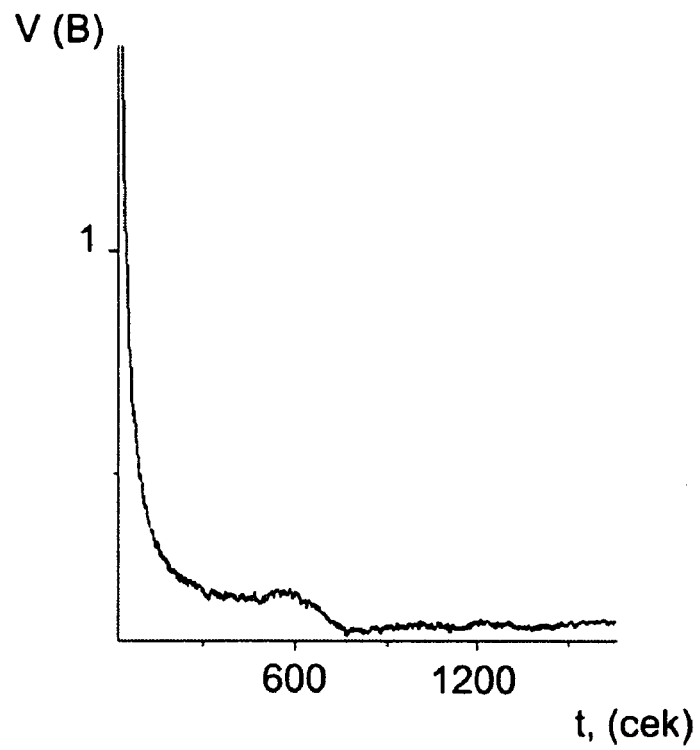
FIG. 21 shows a constant-temperature spectrum of the light emitted by a sample surface activated by low temperature plasma at other conditions then at FIG. 20.
Figure 22:
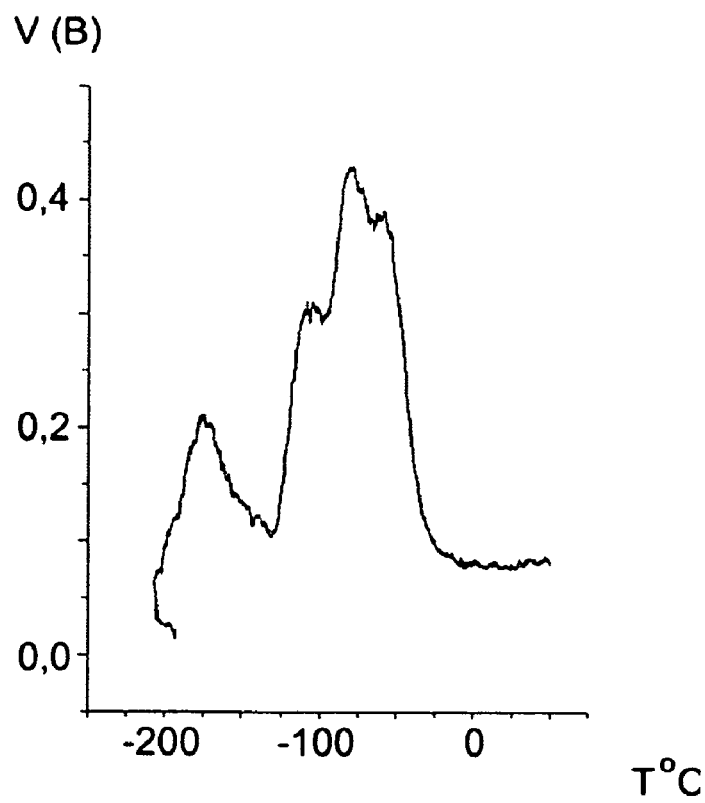
FIG. 22 shows a spectrum of the light emitted by a sample surface activated by low temperature plasma and then heated after emitting shown in FIG. 21 is completed

The overall effect of successive irradiation to the surface layer of a sample of low-sample polyethylene, the sample of which was produced similar to that of Examples 4-6, was investigated for electron, photon and ion beams. The total irradiation power of the pulses was $2.5\times10^{-5}$ W/cm$^2$ per a unit of area investigated on the surface. FIG. 17 shows a thermoluminescence spectrum recorded for the surface layer when the sample was heated.

A comparison of the thermoluminescence spectra recorded for the samples in Examples 4-7, produced under similar conditions but subjected to unit pulses in different combinations, provides a means to base a conclusion about the nature of excitation of the surface states in each example. The temperatures and the energy characteristics of the phase and relaxation transitions occurring at unfreezing of mobility of the excited surface are estimated from the positions of the peaks.

The foregoing descriptions of the specific embodiments of the present invention have been presented for the purposes of illustration and description only. They are not intended to be exhaustive nor are they intended to limit the invention to the precise forms disclosed and, obviously, many modifications and variations are possible in light of the above teaching. The embodiments were chosen and described in order to best explain the principles of the invention and its practical application, to thereby enable others skilled in the art to best utilize the invention and its various embodiments with various modifications as are suited to the particular use contemplated. It is intended that the scope of the invention be defined by the Claims appended hereto and their equivalents. Therefore, the scope of the invention is to be limited only by the following claims.

The invention claimed is:

1. A method for analyzing physical and/or chemical properties of the solid body comprising the activation of said solid body by activating irradiation coming from outside of analyzed solid body, the deactivating of the solid body, and the recording of the spectrum of the energy quanta emitted by the solid body, wherein:
   a. the activating irradiation is used as single pulse and its dose and exposure is chosen in such way that said activating irradiation penetrates not through the whole volume of material but only through the limited surface layer of said solid body without sufficient damage of said surface layer by activating irradiation
   b. termination of said activating irradiation;
   c. after termination of said activating irradiation said solid body is deactivated by keeping the solid body at a constant temperature (isothermal luminescence) and subsequently heating it when the isothermal luminescence is over;
   d. the spectrum of the energy quanta emitted by the surface layer of the solid body, activated by aid activating irradiation, is recorded during the deactivation in such a way that the spectrum of the emitted energy quanta recorded at a constant temperature provides (isothermal Luminescence) data on the loosely coupled states of the surface layer and their half-lives, while the followed thermoluminescence spectrum recorded during the heating gives information on the phase and relaxation transitions in the surface layer.

2. The method as per claim 1, wherein the measuring cycle is repeated at different energies and/or doses of irradiation to receive the information about surface layer structure at different depths (surface tomography).

3. The method as per claim 1, wherein the irradiation pulse activating the investigated surface has the power from 10-5 to 10-3 W/cm2.

4. The method of claim 1, wherein the thermo-luminescence is recorded immediately after activating irradiation is terminated.

5. The method of claim 1, where activating irradiation presents electron beam, atomar beam, molecular beam, ion beam, high energy quanta, low temperature plasma or their combinations.

6. The method of claim 1, wherein the thickness of said surface layer is below ca. 10 μm.

7. The method of claim 1, wherein the thickness of said surface layer is below ca. 1 μm.

8. The method of claim 1, wherein the thickness of said surface layer is below ca. 100 nm.

9. The method as per claim 1, wherein the thickness of said surface layer is below ca. 10 nm.

10. The method as per claim 1, wherein the thickness of said surface layer is below ca. 1 nm.

* * * * *